US009516434B2

(12) United States Patent
Björn et al.

(10) Patent No.: US 9,516,434 B2
(45) Date of Patent: Dec. 6, 2016

(54) MEDICAL DEVICE COUPLING ARRANGEMENT

(71) Applicants: Göran Björn, Onsala (SE); Henrik Fyrlund, Göteborg (SE); Stefan Magnander, Göteborg (SE)

(72) Inventors: Göran Björn, Onsala (SE); Henrik Fyrlund, Göteborg (SE); Stefan Magnander, Göteborg (SE)

(73) Assignee: Cochlear Limited, Macquarie University, NSW (AU)

( * ) Notice: Subject to any disclaimer, the term of this patent is extended or adjusted under 35 U.S.C. 154(b) by 463 days.

(21) Appl. No.: 13/890,358

(22) Filed: May 9, 2013

(65) Prior Publication Data

US 2014/0336447 A1 Nov. 13, 2014

(51) Int. Cl.
*H04R 25/00* (2006.01)
*A61B 19/00* (2006.01)

(52) U.S. Cl.
CPC ......... *H04R 25/606* (2013.01); *H04R 2225/67* (2013.01); *H04R 2460/13* (2013.01)

(58) Field of Classification Search
CPC .............. H04R 25/606; H04R 2460/13; H04R 2225/67; H04R 25/608
USPC ..................... 600/25; 128/899; 381/312, 326
See application file for complete search history.

(56) References Cited

U.S. PATENT DOCUMENTS 3,952,726 A * 4/1976 Hennig et al. .................. 600/30
4,612,915 A * 9/1986 Hough et al. .................. 600/25
7,198,596 B2 4/2007 Westerkull
2007/0053536 A1 3/2007 Westerkull
2009/0252353 A1 10/2009 Parker et al.
2011/0001025 A1 1/2011 Fiedler
2012/0080039 A1 4/2012 Siegert
2012/0302823 A1 11/2012 Andersson et al.
2013/0018218 A1 1/2013 Haller et al.

OTHER PUBLICATIONS

International Search Report and Written Opinion in counterpart International Application No. PCT/IB2014/061306, mailed Sep. 1, 2014, 14 pages.

* cited by examiner

*Primary Examiner* — Samuel Gilbert
(74) *Attorney, Agent, or Firm* — Edell, Shapiro & Finnan, LLC

(57) ABSTRACT

Embodiments presented herein are generally directed to a coupling arrangement for securing an external component to a recipient of an implantable medical device. The coupling arrangement is configured to magnetically couple the external component to a recipient so as to minimize damage to tissue of the recipient adjacent to the coupling arrangement.

30 Claims, 9 Drawing Sheets

MEDICAL DEVICE COUPLING ARRANGEMENT

BACKGROUND

Field of the Invention

The present invention relates generally to medical devices, and more particularly, to a coupling arrangement for a medical device.

Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, direct acoustic stimulators, cochlear implants, auditory brain stimulators, etc.), functional electrical stimulation devices (e.g., implantable pacemakers, defibrillators, etc.), and other implantable medical devices, have been successful in performing life saving and/or lifestyle enhancement functions for a number of years. The types of implantable medical devices and the ranges of functions performed thereby have continued to increase over the years.

Many implantable medical devices include and/or operate in conjunction with external components. When in use, these external components are worn by, or otherwise secured to, the recipient.

SUMMARY

In one aspect, an apparatus is provided. The apparatus comprises an external component and a coupling arrangement configured to magnetically couple the external component to a recipient. As a result of a coupling force generated by the coupling arrangement, a substantially uniform pressure is applied to tissue of the recipient adjacent to the coupling unit.

In another aspect, a coupling arrangement is provided. The coupling arrangement is configured to magnetically couple an external component to a recipient and comprises a first external magnet configured to generate a first magnetic coupling force with a first implantable fixture disposed in the recipient, and a second magnet configured to generate a second magnetic coupling force with a second implantable fixture that is less than the first magnetic coupling force.

In a further aspect, a hearing prosthesis is provided. The hearing prosthesis comprises an implantable component configured to be secured to a recipient's bone, an external component, and a pressure plate detachably connected to the external component. The pressure plate is configured to magnetically couple to the implantable component such that a pressure applied to the tissue of the recipient does not substantially damage the tissue adjacent to the pressure plate.

BRIEF DESCRIPTION OF THE DRAWINGS

Embodiments are described herein in conjunction with the accompanying drawings, in which.

DETAILED DESCRIPTION

Embodiments presented herein are generally directed to a coupling arrangement for securing an external component to a recipient of an implantable medical device. The coupling arrangement is configured to magnetically couple the external component to a recipient such that, as a result of the coupling force, point loads (point pressures) are minimized so as to substantially avoid damage to the recipient's tissue adjacent to the coupling arrangement. Further as a result of the coupling force, a substantially uniform pressure may be applied to the tissue of the recipient adjacent to the coupling arrangement.

There are different types of implantable medical devices having a wide variety of corresponding implantable components that may be partially or fully implanted into a recipient. For example, implantable medical devices may include hearing prostheses (e.g., passive bone conduction devices, active bone conduction devices, mechanical stimulators, cochlear implants, etc.), sensors, implantable pacemakers, defibrillators, functional electrical stimulation devices, catheters, etc. Many of these implantable medical devices include or operate in conjunction with external components that are secured to a recipient. It is to be appreciated that coupling arrangements in accordance with embodiments presented herein may be used in connection with any of the above or other implantable medical devices in which an external component is secured to a recipient. However, merely for ease of description, embodiments are primarily described herein in connection with one exemplary implantable medical device, namely a passive transcutaneous bone conduction device.

Figure 1:
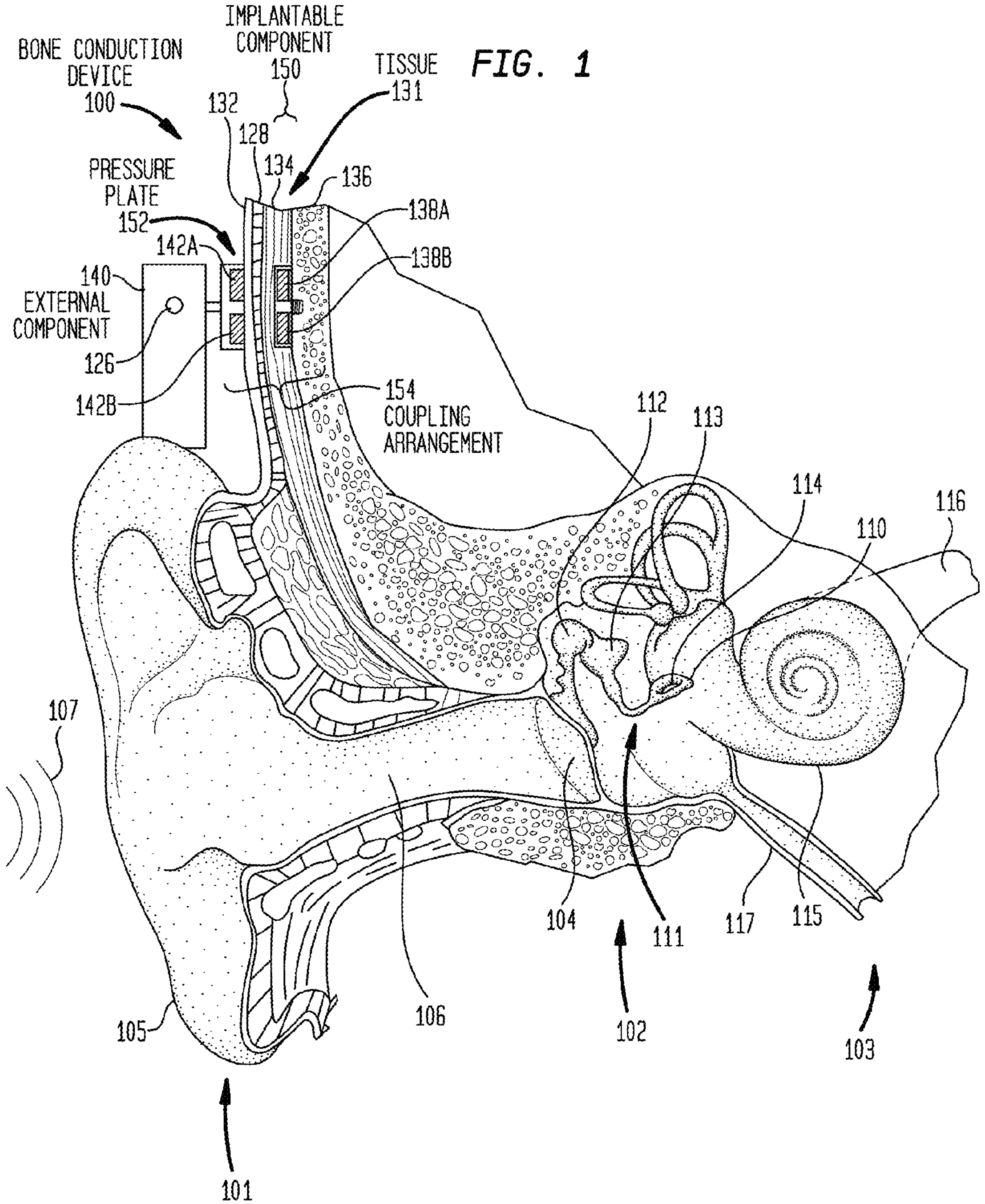
FIG. 1 is a schematic diagram of one embodiment of an exemplary transcutaneous bone conduction device having a coupling arrangement in accordance with embodiments presented herein.

FIG. 1 is a perspective view of a passive transcutaneous bone conduction device 100 in which embodiments presented herein may be implemented. Bone conduction device 100 comprises an external component 140 positioned behind outer ear 101 of the recipient and an internal or implantable component 150 implanted in the recipient.

The external component 140 includes a sound input element 126 to receive sound signals. The sound input element 126 may be, for example, a microphone, telecoil, etc. The sound input element 126 may be located on or in the external component 140, on a cable or tube extending from the external component 140, etc. Alternatively, the sound input element 126 may be subcutaneously implanted in the recipient, or positioned in the recipient's ear. The sound input element 126 may also be a component that receives an electronic signal indicative of sound, such as, for example, from an external audio device.

Bone conduction device 100 is an implantable medical device because, as noted above, it includes at least one implantable component 150 configured to be implanted in the recipient. As shown in FIG. 1 and described further below, the implantable component 150 comprises first and second implantable fixtures 138A and 138B configured to be implanted underneath the recipient's tissue (i.e., skin 132, fat 128, and muscle 134) adjacent to and abutting skull bone 136. In certain embodiments, the first and second implantable fixtures 138A and 138B are magnets or non-magnetized magnetic material (e.g., non-magnetized ferromagnetic or ferromagnetic material).

Bone conduction device 100 also comprises an external pressure plate 152 that is attached to external component 140. Pressure plate 152 comprises a first external magnet 142A and a second external magnet 142B that are configured to magnetically couple to the first implantable fixture 138A and the second implantable fixture 138B, respectively. First and second external magnets 142A and 142B and first and second implantable fixtures 138A and 138B are sometimes collectively referred to herein as a coupling arrangement 154. In general, the coupling arrangement 154 is configured to secure the external component 140 to the recipient such that, absent an external force to remove the external component, the pressure plate 152 will remain in a stationary and aligned position with the implantable component 150. Additionally, as described further below, the coupling arrangement 154 is configured to magnetically couple the external component 140 to the recipient such that, as a result of the coupling force, point loads (point pressures) are minimized so as to avoid damage to the recipient's tissue adjacent to the pressure plate 152. Further as a result of the coupling force, a substantially uniform pressure may be applied to the tissue of the recipient adjacent to the pressure plate 152 (i.e., the tissue between the pressure plate 152 and the implantable component 150).

As shown, the recipient has an outer ear 101, a middle ear 102 and an inner ear 103. In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of the middle ear 102, collectively referred to as the ossicles or ossicular chain 111 and comprising the malleus 112, the incus 113 and the stapes 114. The ossicles 111 of the middle ear 102 serve to filter and amplify acoustic wave 107, causing the oval window 110 to vibrate. Such vibration sets up waves of fluid motion within the cochlea 115 that, in turn, activates hair cells (not shown) that line the inside of the cochlea 115. Activation of the hair cells causes appropriate nerve impulses to be transferred through the spiral ganglion cells and the auditory nerve 116 to the brain (not shown), where they are perceived as sound.

Certain recipients suffer from conductive hearing loss where the normal mechanical pathways of the outer ear 101 and/or the middle ear 102 are impeded, for example, by damage to the ossicular chain 111 or the ear canal 116. With conductive hearing loss, as opposed to sensorineural hearing loss, there is generally no damage to the inner ear 103 or to the auditory nerve 116. Bone conduction devices, such as bone conduction 100, take advantage of the fact that the inner ear 103 of the recipient is fully functional. More specifically, when sound input element 126 receives a sound, an electrical signal representing the sound is provided to a sound processor (not shown) in external component 140. The sound processor processes the electrical signals, and then provides those processed signals to an actuator or transducer (also not shown) in external component 140. The actuator converts the electrical signals into mechanical vibration that is delivered to the recipient via the pressure plate 152 and the implantable component 150. The vibration delivered to the recipient causes movement of the cochlea fluid (perilymph) within the recipient's cochlea 115 to stimulate the hair cells and evoke perception of the sound received at the sound input element 126.

Figure 2A:
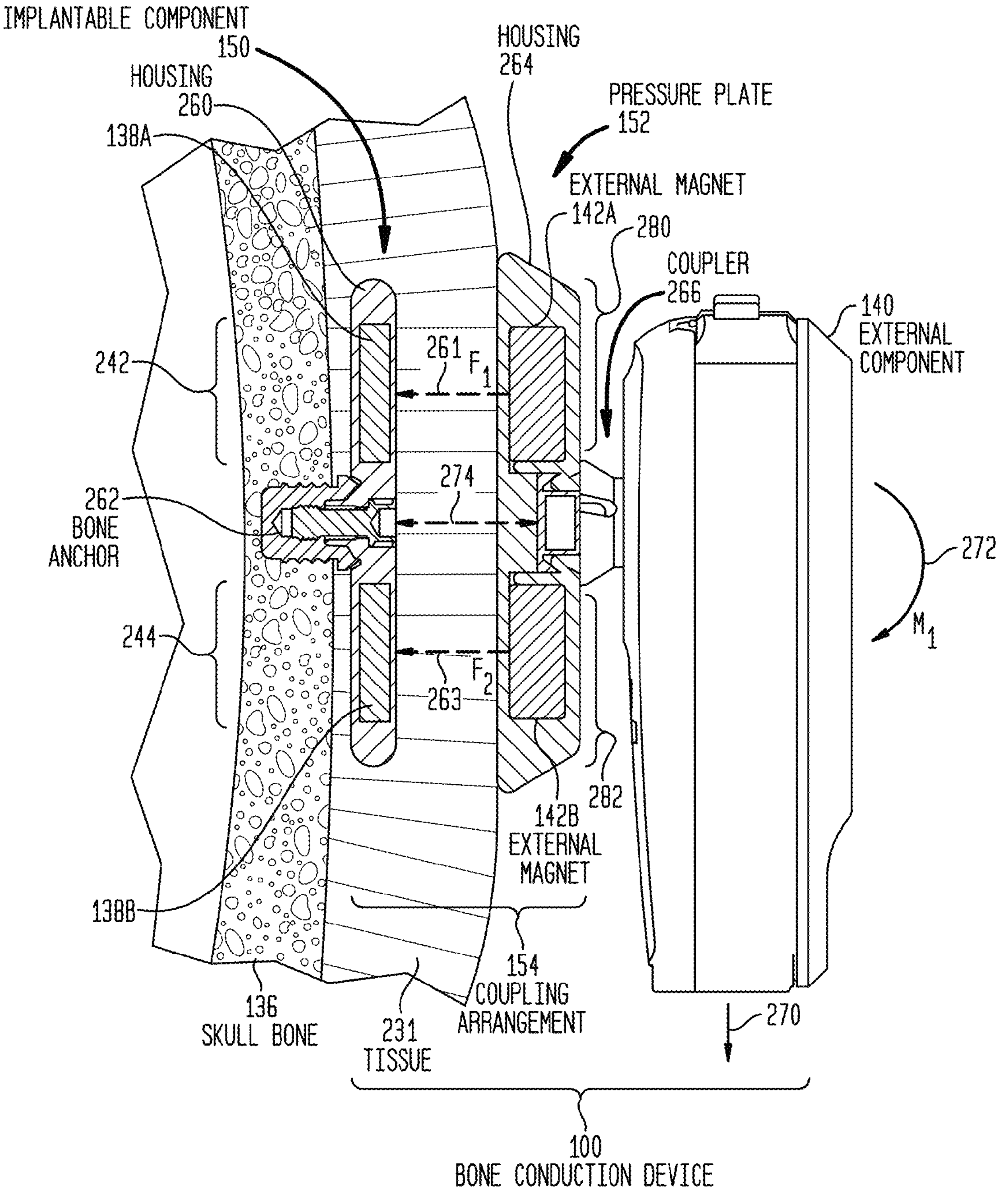
FIG. 2A is a cross-sectional view of the coupling arrangement of FIG. 1.

FIG. 2A is a cross-sectional view illustrating further details of implantable component 150 and pressure plate 152 of bone conduction 100 of FIG. 1. As noted, the implantable component 150 comprises first and second implantable fixtures 138A and 138B. Implantable fixtures 138A and 138B are formed from a magnetic material that generates and/or is reactive to a magnetic field (i.e., a permanent ferrimagnetic or ferromagnetic magnet and/or a non-magnetized ferrimagnetic or ferromagnetic element). However, in the specific embodiments of FIG. 2A, implantable fixtures 138A and 138B are permanent magnets that have opposing magnetic polarities or at least opposing magnetic-polarities on the portions facing the skin of a recipient. For example, the implantable fixture 138A has a magnetic south (negative) polarity, while the implantable fixture 138B has a magnetic north (positive) polarity.

The implantable fixture 138A is referred to herein as the "superior" implantable fixture because, when implanted, it is positioned closer to the top of the head of the recipient than the implantable fixture 138B. Similarly, implantable fixture 138B is referred herein as the "inferior" implantable fixture because it is positioned farther from the top of the head of the recipient than the implantable fixture 138A.

The first and second implantable fixtures 138A and 138B are disposed in a housing 260. The housing 260 is, in this example, a hermetically-sealed and biocompatible housing that separates the potentially toxic material of the implantable fixtures 138A and 138B from the recipient's tissue and body fluid. Attached to, or integrated with, the housing 260 is a bone anchor 262. The bone anchor is a threaded member that screws into the recipient's skull bone 136 (FIG. 1) to secure the housing within the recipient.

Figure 2B:
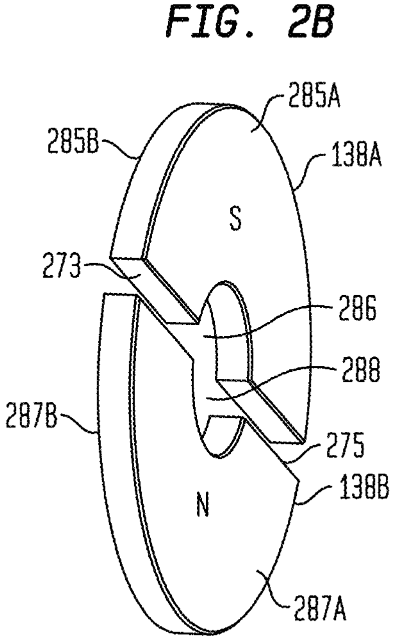
FIG. 2B is a perspective view of the implantable fixtures of FIG. 2A.

FIG. 2B is a perspective view of implantable fixtures 138A and 138B shown separate from housing 260. As shown, the implantable fixture 138A has a generally arcuate shape comprising two generally semicircular surfaces 285A and 285B separated by a substantially uniform distance (thickness). A semicircular notch (cutout) 286 is formed along a linear edge 273 of the implantable fixture 138A. The implantable fixture 138B has a substantially similar generally arcuate shape comprising two generally semicircular surfaces 287A and 287B separated by a substantially uniform distance (thickness). A semicircular notch (cutout) 288 is formed along a linear edge 275 of the implantable fixture 138B.

As noted, and referring again to FIG. 2A, pressure plate 152 comprises first and second external magnets 142A and 142B. The external magnet 142A is referred to herein as the "superior" external magnet because, when worn by the recipient, it is positioned closer to the top of the head of the recipient than the external magnet 142B. Similarly, external magnet 142B is referred herein as the "inferior" external magnet because it is positioned farther from the top of the head of the recipient than the external magnet 142A.

The first and second magnets 142A and 142B are disposed in a housing 264. The housing 264 is attached to the external component 140 via a releasable coupler 266.

Figure 2C:
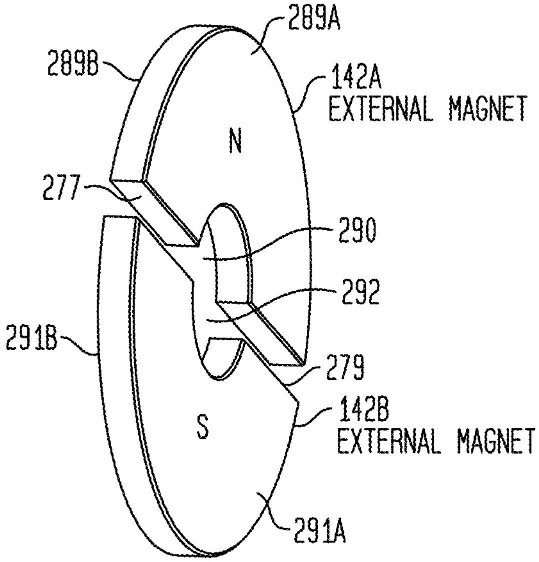
FIG. 2C is a perspective view of the external magnets of FIG. 2A.

FIG. 2C is a perspective view of external magnets 142A and 142B shown separate from housing 264. As shown, the external magnet 142A has a generally arcuate shape comprising two generally semicircular surfaces 289A and 289B separated by a substantially uniform distance (thickness). A semicircular notch (cutout) 290 is formed along a linear edge 277 of the external magnet 142A. The external magnet 142B has a substantially similar generally arcuate shape comprising two generally semicircular surfaces 291A and 291B separated by a substantially uniform distance (thickness). A semicircular notch (cutout) 292 is formed along a linear edge 279 of the external magnet 142B.

In the embodiments of FIGS. 2A-2C, external magnets 142A and 142B are permanent magnets. The external magnets 142A and 142B may have opposing magnetic polarities or at least opposing magnetic-polarities on the portions facing the skin of a recipient. As shown in FIG. 2C, the external magnet 142A has a magnetic north (positive) polarity, while the external magnet 142B has a magnetic south (negative) polarity. In alternative embodiments, external magnets 142A and 142B may be formed from a non-magnetized ferrimagnetic or ferromagnetic element.

As can be seen from FIGS. 2B and 2C, the polarity of the magnets in pressure plate 152 (i.e., superior magnet with positive polarity, inferior magnet with negative polarity) are opposite to the polarity of the magnets in implantable component 150 (i.e., superior magnet with negative polarity, inferior magnet with positive polarity). This specific arrangement ensures that the pressure plate 152 can only be secured to the recipient in a pre-selected orientation. In operation, when the pressure plate 152 (and attached external component 140) is positioned in proximity to the implantable component 150, the external magnet 142A is configured to magnetically couple to implantable fixture 138A and the external magnet 142B is configured to magnetically couple to implantable fixture 138B.

It is known that the mass of an object is a fundamental property of the object (i.e., a measure of the amount of matter in the object). It is also known that the weight of an object is defined as the force of gravity on the object and may be calculated as the mass of the object times the acceleration of gravity. As shown in FIG. 2A, when the external component 140 is worn by the recipient (i.e., when the pressure plate 152 is magnetically coupled to the implantable component 150), gravitational pull exerts a weight force 270 on the external component 140 (i.e., assuming the recipient is standing upright, gravity pulls the external component 140 in an inferior or downward direction). Because the weight force 270 is applied at a distance from the attachment point (i.e., the point of magnetic coupling between the pressure plate 152 and implantable component 150), the weight force causes a moment ($M_1$) 272 to be applied to the external component 140. As known, a "moment" is a measure of the tendency of a force to cause an object to rotate about a specific point or axis. In the example of FIG. 2A, the moment 272 causes external component 152 to rotate around a central axis 274 between the external magnets 142A and 142B and extending through coupler 266.

As a result of the moment 272 and/or variances in the thickness of the recipient's skin and/or tissue, a superior or upper portion 280 of pressure plate 152 will be pulled, or rotate away from, the recipient's tissue 231. However, as the superior portion 280 is pulled away from the tissue 231, an inferior or lower portion of pressure plate 152 will be pushed, or rotate towards, the tissue 231. In conventional arrangements, this results in an unequal application or force or pressure to the recipient's tissue 231 adjacent to the pressure plate 152. More specifically, in conventional arrangements a force or pressure ($F_1$) 261 applied as a result of the magnetic coupling between external magnet 142A and implantable fixture 138A will be less than the force or pressure ($F_2$) 263 applied as a result of the magnetic coupling between external magnet 142B and implantable fixture 138B. In other words, the tissue 231 between inferior portion 282 of pressure plate 152 and an inferior portion 242 of implantable component 150 will be subjected to a greater compressive force and than which is applied to the tissue 231 between superior portion 280 of pressure plate 152 and a superior portion 240 of implantable component 150 (i.e., excessive point loading (point pressures) at the tissue between inferior portion 282 of pressure plate 152 and an inferior portion 242 of implantable component 150). The greater point loading may result in pressure wounds, necrosis, or other problems at the recipient's tissue 231 adjacent to the inferior portion 282 of pressure plate 152.

In accordance with embodiments presented herein, the coupling arrangement 154 is configured to magnetically couple the external component 140 to the recipient such that, as a result of the coupling force, there is a reduction of excessive point loads or point pressures on a recipient's tissue. This reduction in point loads or pressures may reduce damage to the recipient's tissue as a result of a coupling arrangement. Further as a result of the coupling force, a substantially uniform pressure may be applied to the tissue of the recipient adjacent to both the superior and inferior portions of the pressure plate 152. In general, the coupling arrangement 154 is configured to compensate for the moment 272 generated by the weight force 270 on the external component 140 when worn by the recipient and/or variances in the thickness of the recipient's skin and/or tissue.

As described further below, coupling arrangements in accordance with embodiments presented herein, may have a number of different configurations to ensure that a substantially uniform pressure is applied to the tissue of the recipient adjacent the pressure plate. However, in the specific embodiments of FIG. 2A, the uniform pressure is provided by providing external magnets with different magnetic strengths.

More specifically, in the embodiments of FIG. 2A, the superior external magnet 142A has a magnetic strength that is greater than the magnetic strength of inferior external magnet 142B. In general, the superior external magnet 142A has a magnetic strength that is sufficient to prevent superior portion 280 of pressure plate 152 from being pulled away from the recipient tissue 231 as a result of the gravitational pull 270. However, the difference in the magnetic coupling strengths is such that the inferior portion 282 of pressure plate 152 is not pulled away from the recipient's tissue 231. In other words, superior external magnet 142A has a magnetic strength that is sufficient to counteract the moment 272, but that does not create a moment in the opposite direction.

As noted, the coupling arrangement 154 is configured such that a substantially uniform pressure is applied to the recipient's tissue 231 adjacent to the coupling arrangement (i.e., an even pressure is applied to substantially all portions of the tissue 231 between the pressure plate 152 and the implantable component 150). In certain embodiments, the coupling arrangement 154 is configured such that the average (mean) maximum pressure applied to the tissue 231 adjacent to the coupling arrangement is below 0.4 Newtons per square centimeter ($N/cm^2$). In certain arrangements, peak pressures may be momentarily higher than 0.4 $N/cm^2$.

In one theoretical example, the superior magnets (external magnet 142A and implantable fixture 138A) have a magnetic coupling force of approximately 0.8 N. In this example, the inferior magnets (external magnet 142B and implantable fixture 138B) have a magnetic coupling force of approximately 0.25N.

Figure 3:
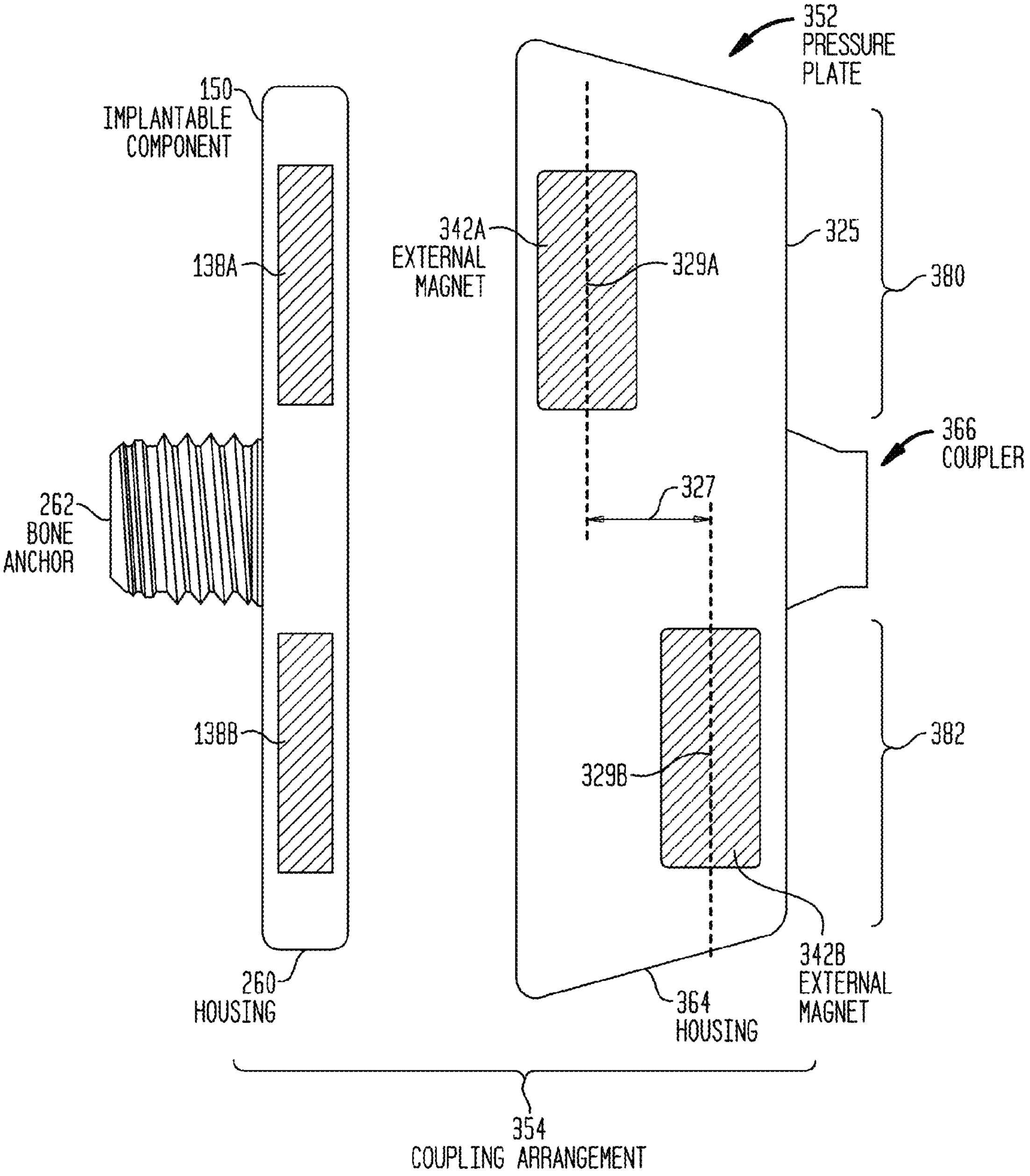
FIG. 3 is a cross-sectional view of a coupling arrangement in accordance with alternative embodiments presented herein.

FIG. 3 is schematic, cross-sectional view of an embodiment of a coupling arrangement 354 in accordance with embodiments presented herein. The coupling arrangement 354 is configured to secure an external component to a recipient such that, as a result of the coupling force, point loads are minimized so as to avoid damage to the recipient's tissue adjacent to the coupling arrangement. Further as a result of the coupling force, a substantially uniform pressure may be applied to the tissue of the recipient adjacent to the coupling arrangement. In the embodiments of FIG. 3, the coupling arrangement 354 comprises an implantable component 150 (as described above with reference to FIGS. 1 and 2A) and an external pressure plate 352. For ease of illustration, the implantable component 150 and the pressure plate 352 are shown spaced from one another and separate from a recipient's tissue and bone.

The pressure plate 352 comprises a superior external magnet 342A and an inferior external magnet 342B that may each have a number of different shapes and sizes. In one specific embodiment, the external magnets 342A and 342B each have a shape as described above with reference to magnets 142A and 142B (i.e., a generally arcuate shape comprising two generally semicircular surfaces separated by a substantially uniform distance with a semicircular notch formed along a linear edge). In the embodiments of FIG. 3, the external magnet 342A has substantially the same shape and size as external magnet 342B.

The magnets 342A and 342B are disposed in a housing 364 that is configured to be attached to an external component (not shown in FIG. 3) via a releasable coupler 366. The housing 366 has a surface 323 that is configured to be positioned abutting the recipient's tissue and a surface 325 that is configured to be positioned in proximity to the external component. Surface 323 is sometimes referred to herein as a tissue-facing surface, while surface 325 is sometimes referred to herein as an external component-facing surface.

In the embodiments of FIG. 3, external magnets 342A and 342A are not substantially aligned with one another, but rather are offset from one another by a distance 327. More specifically, a central axis 329A of external magnet 342A is positioned a distance 327 closer to tissue-facing surface 323 than a central axis 329B of external magnet 342B. Accordingly, since the external magnets 342A and 342B have substantially the same shape and size, when the pressure plate 352 is worn by a recipient, the external magnet 342A will be positioned the distance 327 closer to a recipient's tissue then the external magnet 342B.

In the embodiments of FIG. 3, the external magnet 342A has substantially the same magnetic strength as the external magnet 342B. However, because the external magnet 342A is positioned closer to the recipient's tissue (when in use) than the external magnet 342B, the magnetic coupling between external magnet 342A and implantable fixture 138A will be greater (stronger) than the magnetic coupling between external magnet 342B and implantable fixture 138B. In general, the difference in the magnetic coupling strengths provided by the superior magnets 342A and 138B and that provided by the inferior magnets 342B and 138B may be sufficient to prevent the superior portion 380 of pressure plate 352 from being pulled away from the recipient's tissue as a result of a weight force on an attached external component. However, the difference in the magnetic coupling strengths is such that the inferior portion 382 of pressure plate 352 is not pulled away from the recipient's tissue. In other words, the magnetic coupling provided by superior magnets 342A and 138A has a magnetic strength that is sufficient to counteract a moment created by a weight force on the attached external component, but that does not create a moment in the opposite direction.

Figure 4:
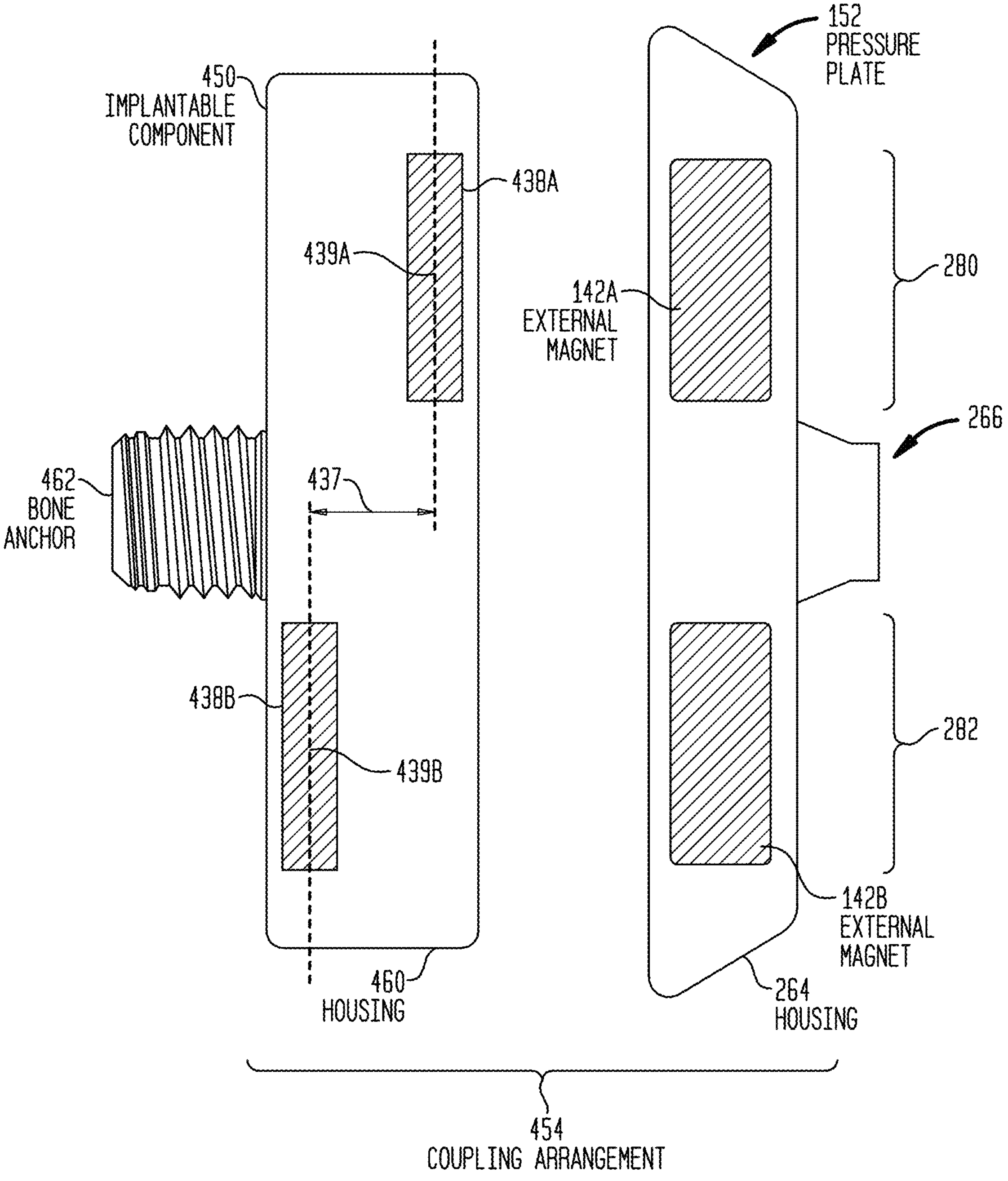
FIG. 4 is a cross-sectional view of a coupling arrangement in accordance with other embodiments presented herein.

FIG. 4 is schematic, cross-sectional view of an embodiment of a coupling arrangement 454 in accordance with embodiments presented herein. The coupling arrangement 454 is configured secure an external component to a recipient such that, as a result of the coupling force, point loads are minimized so as to avoid damage to the recipient's tissue adjacent to the coupling arrangement. Further as a result of the coupling force, a substantially uniform pressure may be applied to the tissue of the recipient adjacent to the coupling arrangement 454. In the embodiments of FIG. 4, the coupling arrangement 454 comprises an implantable component 450 and an external pressure plate 152 (as described above with reference to FIGS. 1 and 2A). For ease of illustration, the implantable component 450 and the pressure plate 152 are shown spaced from one another and separate from a recipient's tissue and bone.

The implantable component 450 comprises a superior implantable fixture 438A and an inferior implantable fixture 438B that may each have a number of different shapes, sizes, and configurations. In one specific embodiment, the implantable fixtures 438A and 438B are each permanent magnets and have a shape as described above with reference to implantable fixtures 138A and 138B (i.e., a generally arcuate shape comprising two generally semicircular surfaces separated by a substantially uniform distance with a semicircular notch formed at a linear edge). In the embodiments of FIG. 4, the implantable fixture 438A has substantially the same shape and size as implantable fixture 438B.

The implantable fixtures 438A and 438B are disposed in a housing 460 that is attached to a bone anchor 462 that is secured to the recipient's skull. The housing 460 has a surface 433 that is configured to be positioned abutting the recipient's tissue. Surface 433 is sometimes referred to herein as a tissue-facing surface.

In the embodiments of FIG. 4, implantable fixtures 438A and 438B are not substantially aligned with one another, but rather are offset from one another by a distance 437. More specifically, a central axis 439A of implantable fixture 438A is positioned a distance 437 closer to tissue-facing surface 433 than a central axis 439B of implantable fixture 438B. Accordingly, since the implantable fixtures 438A and 438B have substantially the same shape and size, when in use the implantable fixture 438A will be positioned the distance 437 closer to a recipient's tissue than the implantable fixture 438B.

In the embodiments of FIG. 4, the implantable fixture 438A has substantially the same magnetic strength as the implantable fixture 438B. However, because the implantable fixture 438A is positioned closer to the recipient's tissue (when in use) than the implantable fixture 438B, the magnetic coupling between external magnet 142A and implantable fixture 438A will be greater than the magnetic coupling between external magnet 142B and implantable fixture 438B. In general, the difference in the magnetic coupling strengths provided by the superior magnets 142A and 438B and that provided by the inferior magnets 142B and 438B may be sufficient to prevent the superior portion 280 of pressure plate 152 from being pulled away from the recipient's tissue as a result of a weight force on an attached external component. However, the difference in the strengths of the magnetic coupling is such that the inferior portion 282 of pressure plate 152 is not pulled away from the recipient's tissue. In other words, the magnetic coupling provided by superior magnets 142A and 438A has a magnetic strength that is sufficient to counteract a moment created by the weight force on an attached external component, but that does not create a moment in the opposite direction.

Figure 5A:
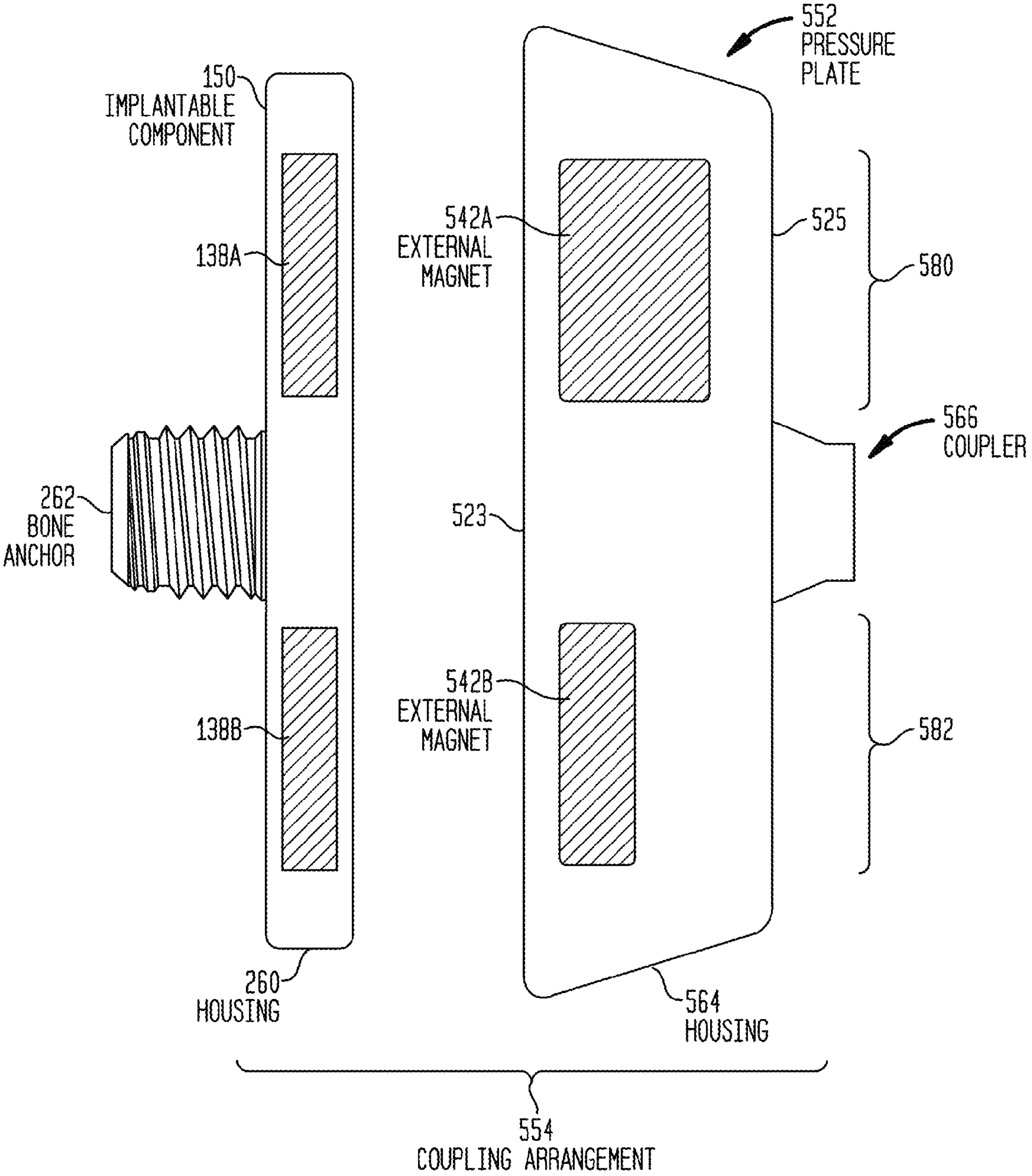
FIG. 5A is a cross-sectional view of a coupling arrangement in accordance with further embodiments presented herein.

FIG. 5A is schematic, cross-sectional view of an embodiment of a coupling arrangement 554 in accordance with further embodiments presented herein. The coupling arrangement 554 is configured to secure an external component to a recipient such that, as a result of the coupling force, point loads are minimized so as to avoid damage to the recipient's tissue adjacent to the coupling arrangement. Further as a result of the coupling force, a substantially uniform pressure may be applied to the tissue of the recipient adjacent to the coupling arrangement 554. In the embodiments of FIG. 5A, the coupling arrangement 554 comprises an implantable component 150 (as described above with reference to FIGS. 1 and 2A) and an external pressure plate 552. For ease of illustration, the implantable component 150 and the pressure plate 552 are shown spaced from one another and separate from a recipient's tissue and bone.

Figure 5B:
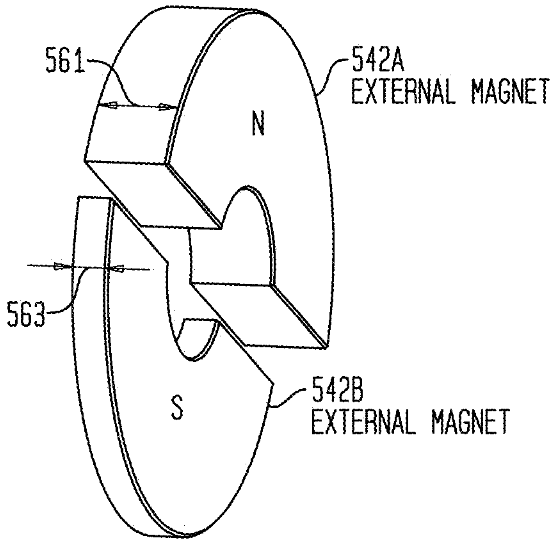
FIG. 5B is a perspective view of the external magnets of FIG. 5A.

The pressure plate 552 comprises a superior external magnet 542A and an inferior external magnet 542B that are disposed in a housing 564 that is configured to be attached to an external component (not shown in FIG. 5A) via a releasable coupler 566. The housing 564 has a tissue-facing surface 523 and an external component-facing surface 525. FIG. 5B is a perspective view of external magnets 542A and 542B shown separate from housing 564.

The external magnets 542A and 542B may each have a number of different shapes and sizes. However, as shown in the specific embodiments of FIGS. 5A and 5B, the external magnets 542A and 542B each have a shape as described above with reference to magnets 142A and 142B (i.e., a generally arcuate shape comprising two generally semicircular surfaces separated by a substantially uniform distance with a semicircular notch formed along a linear edge). In the embodiments of FIGS. 5A and 5B, the external magnet 542A has a substantially larger mass (e.g., larger dimensions, shape, volume, etc.) than external magnet 542B. As shown in FIGS. 5A and 5B, the thickness 561 of external magnet 542A is substantially greater than the thickness 563 of external magnet 542B.

In the embodiments of FIGS. 5A and 5B, the magnetic material forming external magnet 542A has substantially the same magnetic strength as the material forming external magnet 542B. However, because the external magnet 542A has a substantially greater mass than the external magnet 542B, the external magnet 542A will generate a stronger magnetic coupling with implantable fixture 138A than will be will be generated by the external magnet 542B with implantable fixture 138B. In general, the difference in the magnetic coupling strengths provided by the superior magnets 542A and 138B and that provided by the inferior magnets 542B and 138B may be sufficient to prevent the superior portion 580 of pressure plate 552 from being pulled away from the recipient's tissue as a result of a weight force on an attached external component. However, the difference in the strengths of the magnetic couplings is such that the inferior portion 582 of pressure plate 552 is not pulled away from the recipient's tissue. In other words, the magnetic coupling provided by superior magnets 542A and 138A has a magnetic strength that is sufficient to counteract a moment created by the weight force on the attached component, but that does not create a moment in the opposite direction.

The mass difference of FIGS. 5A and 5B between external magnets 542A and 542B are created by increasing the thickness of the superior magnet 542A relative to the inferior magnet 542B. It is to be appreciated that a mass difference can be created in a number of different manners. For example, the height, width, shape, etc. of the superior magnet 542A may be changed relative to the inferior magnet 542B to provide the desired mass difference.

Additionally, FIGS. 5A and 5B illustrate a coupling arrangement 554 in which the mass of the superior external magnet 542A is increased relative to the inferior magnet 542B, but the superior implantable fixture 138A remains the same mass and size as the inferior implantable fixture 138B. In certain embodiments, the mass of the superior implantable fixture 138B may also or alternatively be changed to provide a stronger magnet coupling between the superior magnets. For example, in one embodiment the mass of both the superior magnet 542A and the implantable fixture 138A may be increased relative to the mass of the inferior magnet 542B and the implantable fixture 138B, respectively. In an alternative example, only the mass of the implantable fixture 138A is increased relative to the implantable fixture 138B and the mass of the superior external magnet 542A remains substantially the same as the mass of the inferior external magnet 542B.

Figure 6:
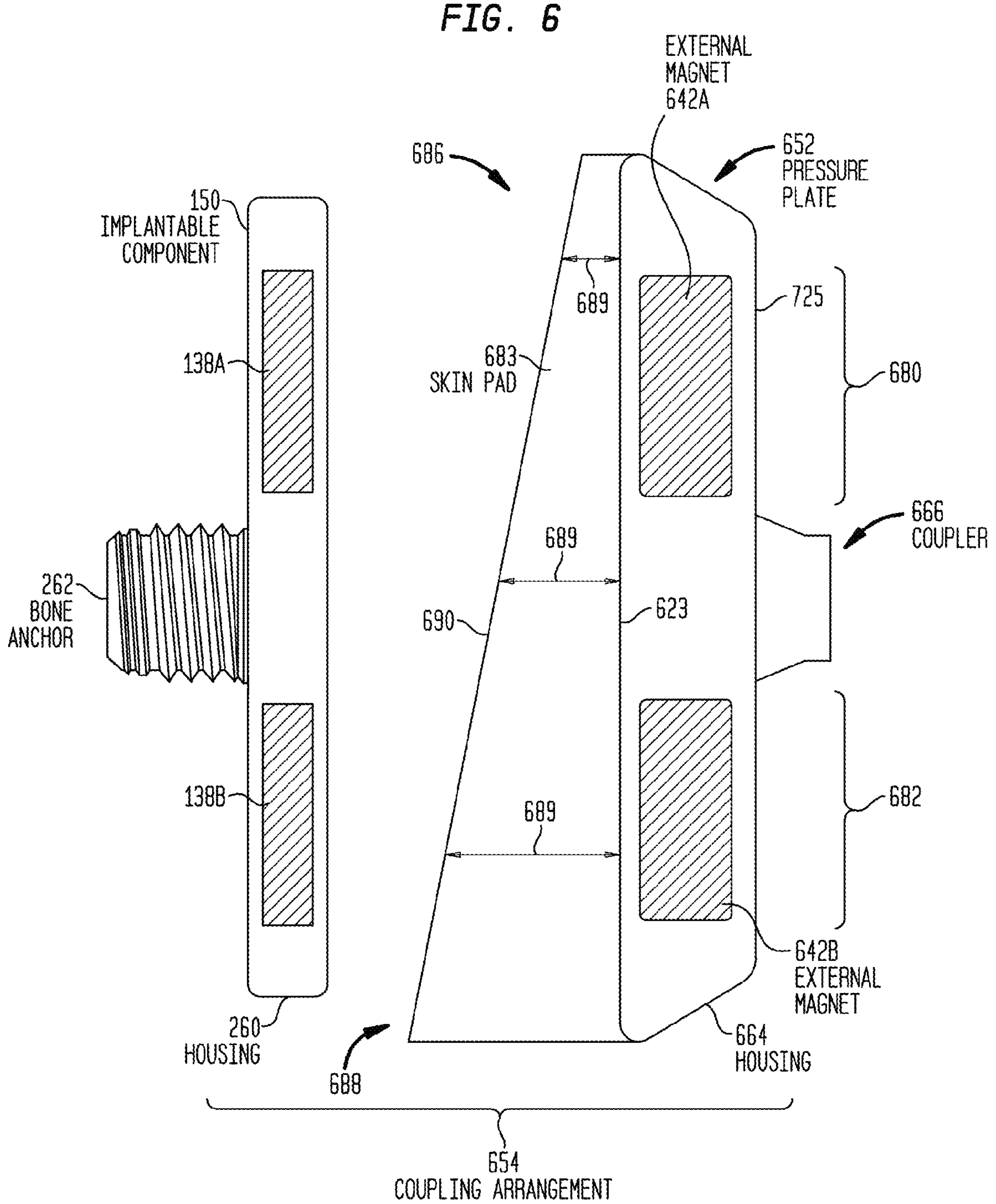
FIG. 6 is a cross-sectional view of a coupling arrangement in accordance with alternative embodiments presented herein.

FIG. 6 is schematic, cross-sectional view of an embodiment of a coupling arrangement 654 in accordance with further embodiments presented herein. The coupling arrangement 654 is configured to secure an external component to a recipient such that, as a result of the coupling force, point loads are minimized so as to avoid damage to the recipient's tissue adjacent to the coupling arrangement. Further as a result of the coupling force, a substantially uniform pressure may be applied to the tissue of the recipient adjacent to the coupling arrangement 654. In the embodiments of FIG. 6, the coupling arrangement 654 comprises an implantable component 150 (as described above with reference to FIGS. 1 and 2A) and an external pressure plate 652. For ease of illustration, the implantable component 150 and the pressure plate 652 are shown spaced from one another and separate from a recipient's tissue and bone.

The pressure plate 652 comprises a superior external magnet 642A and an inferior external magnet 642B that may each have a number of different shapes and sizes. In one specific embodiment, the external magnets 642A and 642B each have a shape as described above with reference to magnets 142A and 142B (i.e., a generally arcuate shape comprising two generally semicircular surfaces separated by a substantially uniform distance with a semicircular notch formed along a linear edge). In the embodiments of FIG. 6, the external magnet 642A has substantially the same shape and size as external magnet 642B and the magnets are substantially aligned with one another. Additionally, the external magnet 642A has substantially the same magnetic strength as the external magnet 642B.

The magnets 642A and 642B are disposed in a housing 664 that is configured to be attached to an external component (not shown in FIG. 6) via a releasable coupler 666. The housing 664 has a tissue-facing surface 623 and an external component-facing surface 625. Attached to the tissue-facing surface 623 of pressure plate 652 is a skin pad 683 that is formed from a compressible material (e.g., foam, a soft polymer, etc.). In the embodiments of FIG. 6, the skin pad 683 is generally wedged-shaped with a superior end 686 positioned adjacent to a superior portion 680 of pressure plate 652 and an inferior end 688 positioned adjacent to an inferior portion 682 of the pressure plate. The thickness 689 of the skin pad 683 decreases from a maximum at the inferior end 688 to a minimum at the superior end 686.

When worn by a recipient, the outer surface 690 of skin pad 683 will abut the recipient's skin and, because the thickness of the skin pad 683 decreases from the inferior end 688 to the superior end 686, the inferior portion 682 of the pressure plate 652 will be positioned farther from the skin than the superior portion of the pressure plate 652. In other words, the wedge shape of the skin pad 683 functions as a spacer that results in the external magnet 642A (in superior portion 680) being positioned closer to the skin than the external magnet 642B (in inferior portion 682). Because the external magnet 642A is positioned closer to the recipient's tissue (when in use) than the external magnet 642B, the magnetic coupling between external magnet 642A and implantable fixture 138A will be greater than the magnetic coupling between external magnet 642B and implantable fixture 138B. In general, the difference in the magnetic coupling strengths provided by the superior magnets 642A and 138B and that provided by the inferior magnets 642B and 138B may be sufficient to prevent the superior portion 680 of pressure plate 652 from being pulled away from the recipient's tissue as a result of a weight force on an attached external component, but such that the inferior portion 682 of pressure plate 652 is not pulled away from the recipient's tissue. In other words, the magnetic coupling provided by superior magnets 642A and 138A has a magnetic strength that is sufficient to counteract a moment created by the weight force on the attached component, but that does not create a moment in the opposite direction.

Figure 7:
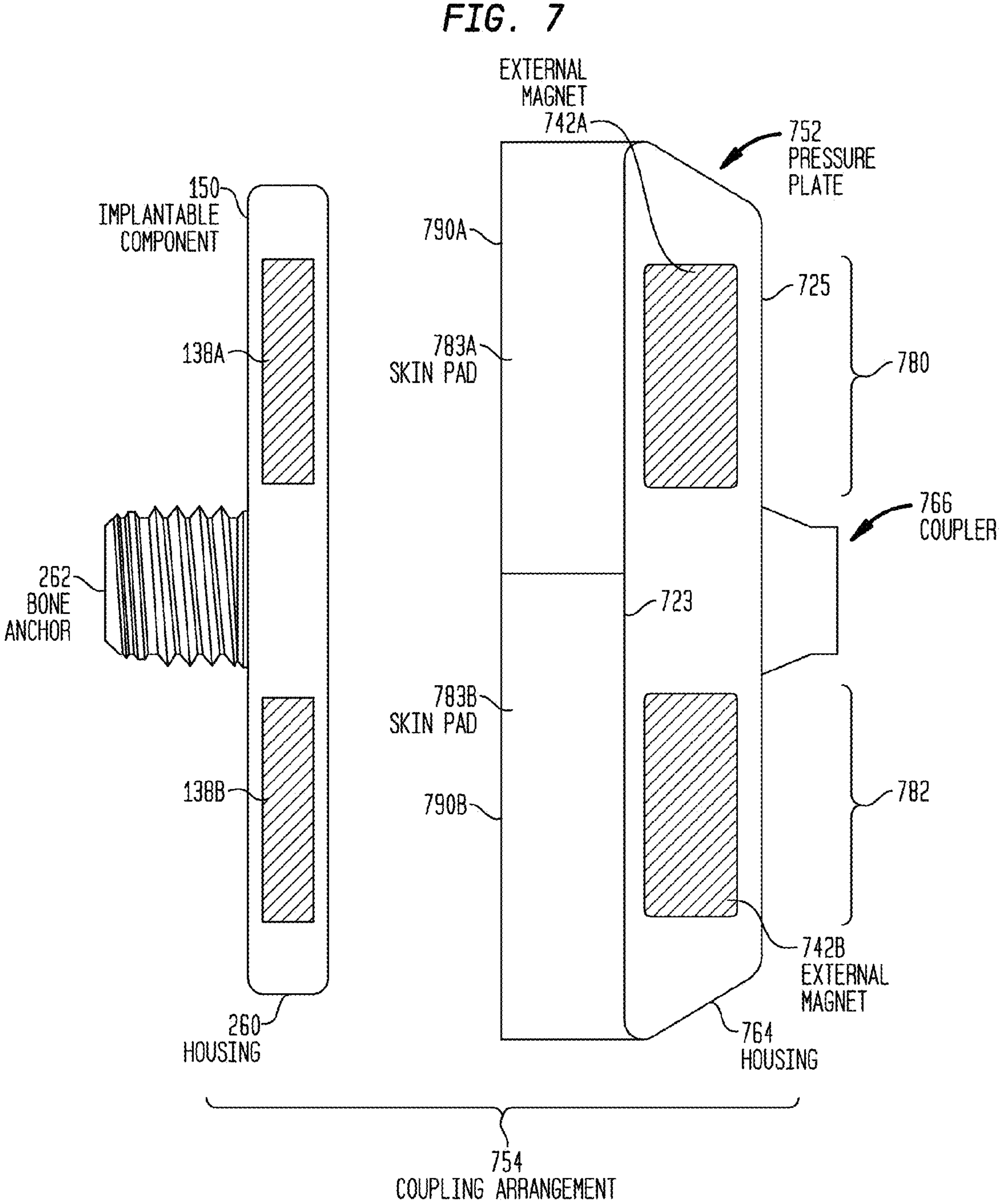
FIG. 7 is a cross-sectional view of a coupling arrangement in accordance with other embodiments presented herein.

FIG. 7 is schematic, cross-sectional view of an embodiment of a coupling arrangement 754 in accordance with further embodiments presented herein. The coupling arrangement 754 is configured to secure an external component to a recipient such that, as a result of the coupling force, point loads are minimized so as to avoid damage to the recipient's tissue adjacent to the coupling arrangement. Further as a result of the coupling force, a substantially uniform pressure may be applied to the tissue of the recipient adjacent to the coupling arrangement 754. In the embodiments of FIG. 7, the coupling arrangement 754 comprises an implantable component 150 (as described above with reference to FIGS. 1 and 2A) and an external pressure plate 752. For ease of illustration, the implantable component 150 and the pressure plate 752 are shown spaced from one another and separate from a recipient's tissue and bone.

The pressure plate 752 comprises a superior external magnet 742A and an inferior external magnet 742B that may each have a number of different shapes and sizes. In one specific embodiment, the external magnets 742A and 742B each have a shape as described above with reference to magnets 142A and 142B (i.e., a generally arcuate shape comprising two generally semicircular surfaces separated by a substantially uniform distance with a semicircular notch formed along a linear edge). In the embodiments of FIG. 7, the external magnet 742A has substantially the same shape and size as external magnet 742B and the magnets are substantially aligned with one another. Additionally, the external magnet 742A has substantially the same magnetic strength as the external magnet 742B.

The magnets 742A and 742B are disposed in a housing 764 that is configured to be attached to an external component (not shown in FIG. 7) via a releasable coupler 766. The housing 764 has a tissue-facing surface 723 and an external component-facing surface 725. Attached to the tissue-facing surface 723 of pressure plate 752 are two skin pads 783A and 783B that are each formed from a compressible material (e.g., foam, a soft polymer, etc.). Skin pad 783A is positioned adjacent to a superior portion 780 of the pressure plate 752, while skin pad 783B is positioned adjacent to an inferior portion 782 of the pressure plate. In the embodiments of FIG. 6, the skin pad 783A is formed from a material that is more compressible that the material used to form skin pad 783B. That is, skin pad 783B is stiffer than skin pad 783A.

When worn by a recipient, the outer surfaces 790A and 790B of skin pads 783A and 783B, respectively, will abut the recipient's skin and pressure will be applied (between the pressure plate 752 and the skin) that compresses the skin pads 783A and 783B. However, because of the different material properties of the skin pads 783A and 783B, the skin pad 783A will compress more than the skin pad 783B. Accordingly, the inferior portion 782 of the pressure plate 752 will be positioned farther from the skin than the superior portion 780 of the pressure plate 752. In other words, the stiffness difference between skin pads 783A and 783B results in the external magnet 742A (in superior portion 780) being positioned closer to the skin than the external magnet 742B (in inferior portion 782). Because the external magnet 742A is positioned closer to the recipient's tissue (when in use) than the external magnet 742B, the magnetic coupling between external magnet 742A and implantable fixture 138A will be greater than the magnetic coupling between external magnet 742B and implantable fixture 138B. In general, the difference in the magnetic coupling strengths provided by the superior magnets 742A and 138B and that provided by the inferior magnets 742B and 138B may be sufficient to prevent the superior portion 780 of pressure plate 752 from being pulled away from the recipient's tissue as a result of a weight force on an attached external component, but such that the inferior portion 782 of pressure plate 752 is not pulled away from the recipient's tissue. In other words, the magnetic coupling provided by superior magnets 742A and 138A has a magnetic strength that is sufficient to counteract a moment created by the weight force on the attached component, but that does not create a moment in the opposite direction.

FIGS. 2A-7 illustrate coupling arrangements in accordance with different embodiments presented herein. It is to be appreciated that the above embodiments are not mutually exclusive and that the different embodiments may be used with one another in various combinations.

Additionally, embodiments have been primarily described above with reference to the use of a coupling arrangement with a passive transcutaneous bone conduction device. However, as noted above, coupling arrangements presented herein may be used with other implantable medical devices having or operating with an external component that is to be secured to the recipient.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An apparatus comprising:
an external component;
a coupling arrangement comprising a pressure plate having a skin-facing surface with superior and inferior portions, wherein the coupling arrangement is configured to magnetically couple the external component to a recipient; and
at least one compressible skin pad comprising superior and inferior portions attached to the superior and inferior portions of the skin-facing surface of the pressure plate, respectively, wherein the inferior portion of the at least one skin pad has a stiffness that is greater than a stiffness of the superior portion of the at least one skin pad.

2. The apparatus of claim 1, wherein the coupling arrangement is configured to compensate for a moment applied to the external component as a result of weight force when the external component is worn in an upright position by the recipient.

3. The apparatus of claim 1, wherein the coupling arrangement is configured to compensate for a moment applied to the external component when worn by the recipient as a result of variances in thickness of skin of the recipient.

4. The apparatus of claim 1, wherein the coupling arrangement and skin pad are configured such that a uniform average pressure of less than 0.4 Newtons per square centimeter ($N/cm^2$) is applied to the tissue of the recipient adjacent to the coupling arrangement.

5. The apparatus of claim 1, wherein the coupling arrangement and skin pad are configured such that a point pressure of less than 0.5 Newtons per square centimeter ($N/cm^2$) is applied to the tissue of the recipient adjacent to the coupling arrangement.

6. The apparatus of claim 1, wherein the coupling arrangement comprises:
an implantable component disposed in the recipient comprising:
a first implantable fixture, and
a second implantable fixture; and
wherein the pressure plate comprises:
a first external magnet configured to be magnetically coupled to the first implantable fixture; and
a second external magnet configured to be magnetically coupled to the second implantable fixture,
wherein a strength of a magnetic coupling between the first external magnet and the first implantable fixture is greater than a strength of a magnetic coupling between the second external magnet and the second implantable fixture.

7. The apparatus of claim 6, wherein the first and second external magnets are co-planar with one another and wherein the first external magnet has a magnetic strength that is greater than a magnetic strength of the second external magnet.

8. The apparatus of claim 6, wherein the first and second implantable fixtures are co-planar magnets and wherein the first implantable fixture has a magnetic strength that is greater than a magnetic strength of the second implantable fixture.

9. The apparatus of claim 6, wherein the first and second external magnets are offset from one another such that the first magnet is configured to be positioned closer to the tissue of the recipient than the second external magnet.

10. The apparatus of claim 9, wherein the first external magnet has a magnetic strength that is greater than a magnetic strength of the second external magnet.

11. The apparatus of claim 6, wherein the first and second implantable fixtures are offset from one another such that the first implantable fixture is configured to be positioned closer to skin of the recipient than the second implantable fixture.

12. The apparatus of claim 6, wherein the first and second implantable fixtures each have a polarity, and wherein a polarity of the first and second magnets and the polarity of the first and second implantable fixtures are such that the pressure plate can only be secured to the recipient in a pre-selected orientation.

13. The apparatus of claim 1, wherein the at least one skin pad has a wedge shape.

14. The apparatus of claim 1, wherein the at least one skin pad comprises:
a first compressible skin pad attached to the superior portion of the skin-facing surface of the pressure plate; and
a second compressible skin pad attached to the inferior portion of the skin-facing surface of the pressure plate,
wherein the second compressible skin pad has a stiffness that is greater than a stiffness of the first compressible skin pad.

15. The apparatus of claim 1, wherein the pressure plate is detachably connected to the external component.

16. A coupling arrangement configured to magnetically couple an external component to a recipient comprising:
a pressure plate having superior and inferior portions;
a first external magnet disposed in the superior portion of the pressure plate;
a second external magnet disposed in the inferior portion of the pressure plate;
a first implantable magnet disposed in the recipient and configured to generate a first magnetic coupling force with the first external magnet;
a second implantable magnet disposed in the recipient and configured to generate a second magnetic coupling force with the second external magnet;
wherein the first implantable magnet has a magnetic strength that is greater than a magnetic strength of the second implantable magnet,
wherein the first magnetic coupling force is greater than the second magnetic coupling force by an amount that results in application of a uniform average pressure to tissue of the recipient adjacent to the coupling arrangement when the external component is mechanically attached to the coupling arrangement and worn by the recipient in an upright position.

17. The coupling arrangement of claim 16, wherein gravitational pull on the external component generates a moment when the external component is worn by the recipient in the upright position, and wherein the first magnetic coupling force is greater than the second magnetic coupling force by an amount that compensates for the moment generated by the gravitational pull on the external component when worn by the recipient in the upright position.

18. The coupling arrangement of claim 16, wherein the coupling arrangement is configured such that a uniform average pressure of less than 0.4 Newtons per square centimeter ($N/cm^2$) is applied to ] tissue of the recipient adjacent to the coupling arrangement.

19. The coupling arrangement of claim 16, wherein the coupling arrangement is configured such that a point pressure of less than 0.5 Newtons per square centimeter ($N/cm^2$) is applied to ] tissue of the recipient adjacent to the coupling arrangement.

20. The coupling arrangement of claim 16, wherein the first and second external magnets are co-planar with one another and wherein the first external magnet has a magnetic strength that is greater than a magnetic strength of the second external magnet.

21. The coupling arrangement of claim 16, further comprising:

a compressible skin pad comprising superior and inferior portions attached to the superior and inferior portions of pressure plate, respectively, wherein the superior portion of the configured to compress a greater amount than the inferior portion of the skin pad.

22. The coupling arrangement of claim 16, wherein the first and second external magnets are offset from one another such that the first external magnet is configured to be positioned closer to tissue of the recipient than the second external magnet.

23. The coupling arrangement of claim 16, wherein the first and second implantable magnets are offset from one another such that the first implantable magnet is configured to be positioned closer to skin of the recipient than the second implantable magnet.

24. A hearing prosthesis, comprising:

an implantable component configured to be secured to a recipient's bone and comprising first and second co-planar implantable magnets, wherein the first implantable magnet has a magnetic strength that is greater than a magnetic strength of the second implantable magnet;

an external component including a pressure plate comprising at least one external magnetic element configured to magnetically couple to the first and second co-planar implantable magnets disposed in the recipient, wherein the magnetic coupling force between the first implantable magnet and the magnetic element is greater than the coupling force between the second implantable magnet and the magnetic element by an amount that results in application of a uniform average pressure to tissue of the recipient adjacent to the pressure plate when the external component is worn by a recipient in an upright position.

25. The hearing prosthesis device of claim 24, wherein the first and second co-planar implantable magnets generate first and second magnetic coupling forces that compensate for a moment generated by weight force on the external component when worn by the recipient.

26. The hearing prosthesis of claim 24, wherein the magnetic strengths of the first and second implantable magnets are such that a uniform average pressure of less than 0.4 Newtons per square centimeter ($N/cm^2$) is applied to the tissue of the recipient located between the pressure plate and the implantable component.

27. The hearing prosthesis of claim 24, further comprising:

at least one compressible skin pad comprising superior and inferior portions attached to superior and inferior portions of a skin facing surface of the pressure plate, respectively, wherein the inferior portion of the at least one skin pad has a stiffness that is greater than a stiffness of the superior portion of the at least one skin pad.

28. A hearing prosthesis, comprising:

an implantable component configured to be secured to a recipient's bone and comprising first and second co-planar implantable magnets, wherein the first implantable magnet has a magnetic strength that is greater than a magnetic strength of the second implantable magnet;

an external component including a pressure plate comprising at least one external magnetic element configured to magnetically couple to the first and second co-planar implantable magnets disposed in the recipient; and a compressible skin pad comprising superior and inferior portions attached to superior and inferior portions of the pressure plate, respectively, wherein:

(i) the superior portion of the skin pad configured to compress a greater amount than the inferior portion of the skin pad, or (ii) the inferior portion of the at least one skin pad has a stiffness that is greater than a stiffness of the superior portion of the at least one skin pad.

29. The coupling arrangement of claim 28, wherein the superior portion of the skin pad configured to compress a greater amount than the inferior portion of the skin pad.

30. The hearing prosthesis of claim 28, wherein the inferior portion of the at least one skin pad has a stiffness that is greater than a stiffness of the superior portion of the at least one skin pad.

* * * * *